United States Patent [19]
Kelly et al.

[11] Patent Number: 5,269,300
[45] Date of Patent: Dec. 14, 1993

[54] AUTOMATIC SENSITIVITY CONTROL IN AN IMPLANTABLE CARDIAC RHYTHM MANAGEMENT SYSTEM

[75] Inventors: David W. Kelly, Vadnais; Carol G. Stadler, Shoreview; Robert Dreher, Roseville, all of Minn.

[73] Assignee: Cardiac Pacemakers, Inc., St. Paul, Minn.

[21] Appl. No.: 921,661

[22] Filed: Jul. 30, 1992

[51] Int. Cl.$^5$ ............................................. A61N 1/37
[52] U.S. Cl. ...................................................... 607/4
[58] Field of Search ...... 128/419 PG, 419 D, 419 PT

[56] References Cited

U.S. PATENT DOCUMENTS

| | | | |
|---|---|---|---|
| 4,708,144 | 11/1987 | Hamilton et al. | 128/419 PG |
| 4,819,643 | 4/1989 | Menken | 128/419 PG |
| 4,827,934 | 5/1989 | Ekwall | 128/419 PG |
| 5,117,824 | 6/1992 | Keimel et al. | 128/419 PG |

Primary Examiner—William E. Kamm
Assistant Examiner—Kennedy J. Schaetzle
Attorney, Agent, or Firm—Keck, Mahin & Cate

[57] ABSTRACT

A method and apparatus for automatically adjusting the sensing threshold in an automatic implantable cardioverter/defibrillator with pacing capability. Fixed sensitivity is used for a specified interval following each pacing pulse and automatic sensitivity adjustment is used when spontaneous cardiac depolarization is detected. For spontaneous cardiac depolarization, the sensing threshold is automatically adjusted to a value proportional to the amplitude of the sensed cardiac signal. The sensing threshold continuously decreases between sensed cardiac depolarizations, ensuring that a lower level cardiac signal will be detected. When a pacing pulse is delivered, the sensing threshold is set to a fixed value and held at that value for a predetermined period of time such that the sensing threshold will not be affected by the cardiac response evoked by the pacing pulse. At the end of the predetermined period of time, the sensing threshold is decreased as it would following a spontaneous cardiac depolarization.

4 Claims, 2 Drawing Sheets

AUTOMATIC SENSITIVITY CONTROL IN AN IMPLANTABLE CARDIAC RHYTHM MANAGEMENT SYSTEM

BACKGROUND OF THE INVENTION

The present invention relates to a method and apparatus for automatically adjusting the sensing threshold in an automatic implantable cardioverter/defibrillator with pacing capability.

In the field of cardiac rhythm control systems, such as implantable cardioversion/defibrillation and pacing, dangerous cardiac rhythms (bardycardia, tachycardia or fibrillation) are commonly detected by measuring the time interval between consecutive cardiac depolarizations. An implantable pacemaker, defibrillator, or external heart monitoring device detects cardiac depolarizations when the sensed cardiac signal exceeds a predetermined amplitude level. The predetermined amplitude level is known as the "sensitivity threshold". The sensing threshold may be fixed, or it may vary over time.

There are extreme variations in cardiac signal amplitude during certain arrhythmias, such as polymorphic tachycardia and fibrillation. Therefore, a fixed sensing threshold may not be appropriate for detecting these arrhythmias. The problem is further complicated when the implantable device delivers pacing pulses to the heart; these pulses cause evoked responses which are quite high in amplitude as compared to normal cardiac depolarizations.

Two prior approaches to compensate for these problems are known. One is to fix the sensing threshold at a value determined by the attending physician after careful study of the variety of amplitudes in cardiac signal activity experienced by a patient; the sensing threshold is programmed into the implantable device. Any cardiac signal larger than the programmed sensing threshold is considered a cardiac depolarization.

The difficulty with this approach is in setting the sensing threshold. If the sensing threshold is too high and the signal amplitude decreases significantly, as is often the case in fibrillation, the device may not sense the arrhythmia. If the sensing threshold is set too low, the device may over-sense. For example, a system designed to detect ventricular depolarizations (R-waves) may erroneously detect atrial depolarizations (P-waves) or ventricular recovery (T-waves). Filtering may help eliminate the erroneous detection of the P-waves and T-waves, but if the pass band of the filter is too narrow, it may also eliminate detection of the fibrillation signals.

A second approach is to set the sensing threshold proportional to the amplitude of a sensed cardiac signal each time a cardiac depolarization is sensed. The sensing threshold is then allowed to decrease over time between consecutively sensed cardiac cycles so that in the event a sensed cardiac signal amplitude decreases significantly, the device is still able to detect the lower level cardiac signals.

The problem with the second approach is that it becomes difficult to adjust the sensing threshold to an appropriate level if the patient requires pacing due to bradycardia. FIG. 1 illustrates the response of such a system that senses R-waves according to this method. The sensing threshold is adjusted to one-half of the R-wave amplitude when an R-wave is sensed. However, the evoked response due to the first pacing pulse causes the sensing threshold to be set so high that a second spontaneous R-wave is not sensed. Because the system did not sense the second spontaneous R-wave, a pacing pulse is delivered to the patient inappropriately.

SUMMARY OF THE INVENTION

It is a primary object of the present invention to overcome the aforementioned problems by providing a method for automatically adjusting the sensing threshold in an automatic implantable cardioverter/defibrillator with pacing capability.

Briefly, the present invention relates to combining the features of a fixed sensing threshold approach and a variable sensing threshold approach. Fixed sensitivity is used for a specified interval following each pacing pulse and automatic sensing threshold adjustment is used when spontaneous cardiac depolarization is detected. That is, for spontaneous cardiac depolarization, the sensing threshold is automatically adjusted to a value proportional to the amplitude of the sensed cardiac signal. The sensing threshold continuously decreases between sensed cardiac depolarizations, ensuring that a lower level cardiac signal will be detected. When a pacing pulse is delivered, the sensing threshold is set to a fixed value and held at that value for a predetermined period of time such that the sensitivity will not be affected by the cardiac response evoked by the pacing pulse. At the end of the predetermined period of time, the sensing threshold begins to decrease as it would following a spontaneous cardiac depolarization.

The above and other objects and advantages will become more readily apparent when reference is made to the following description taken in conjunction with the accompanying drawings

DETAILED DESCRIPTION OF THE DRAWINGS

Figure 1:
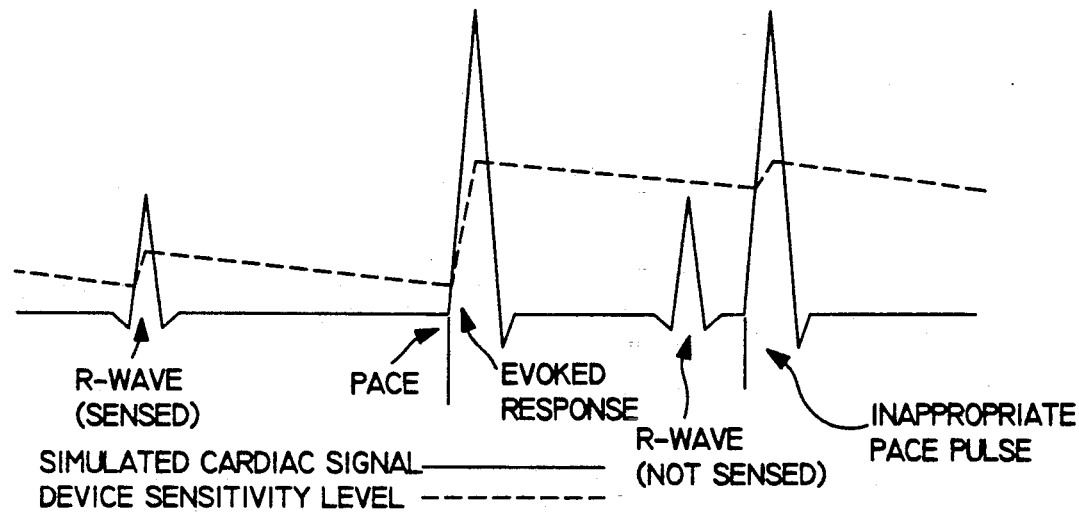
FIG. 1 is a graphical representation of the sensing threshold response in a prior art implantable cardioverter/defibrillator.
Figure 2:
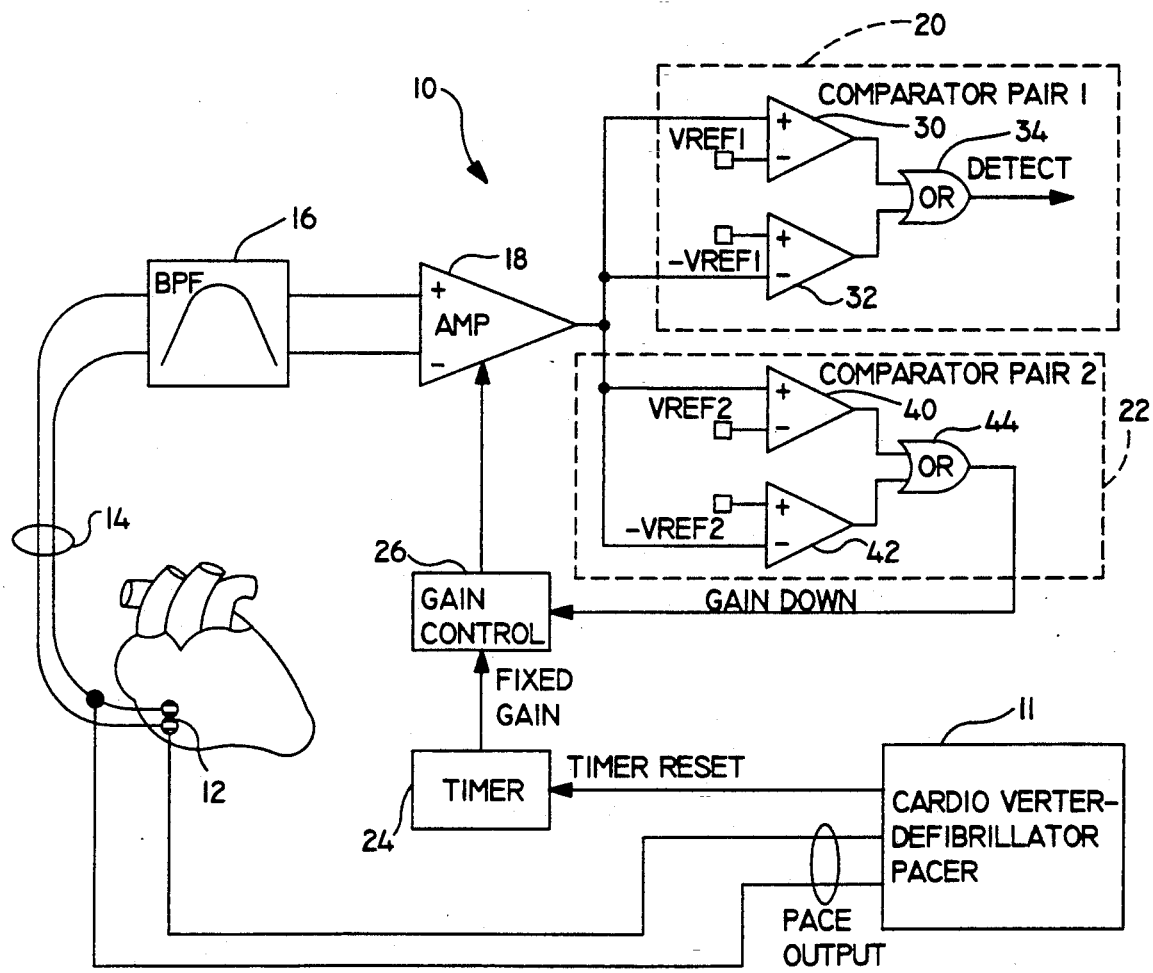
FIG. 2 is a block diagram of the circuitry for controlling the sensing threshold according to the present invention.

Referring to FIG. 2, a block diagram of a system for controlling the sensing threshold in accordance with the present invention is shown generally at 10. The system 10 is designed to detect R-waves for use in measuring the cardiac cycle time. The cardiac cycle time may then be evaluated for the presence of dangerous tachyarrhythmias or the need for bradycardia pacing.

The system 10 may be included as part of a fully implantable cardiac rhythm management system or as part of an external cardiac treatment system. In this regard, the block 11 represents a cardioverter/pacer having pacing capabilities connected to system 10, but it is to be understood that certain of the circuits which are shown as part of the system 10 may be already incorporated as part of block 11.

Implanted electrodes 12 and associated leads 14 supply the system with the sensed cardiac signals The electrodes 12 may also be of the type capable of pacing and defibrillating/cardioverting the heart.

The sensed cardiac signals are fed to a block of circuitry which includes a bandpass filter 16, an amplifier 18, first and second comparator pair circuits 20 and 22, a timer 24 and a gain control circuit 26. The bandpass filter 16 receives the sensed cardiac signals and filters the signal to isolate R-waves from other cardiac signals and noise. The amplifier 18 is a variable gain amplifier and amplifies the output of the bandpass filter 16, which should be an R-wave. The amplifier 18, comparator pair circuits 20 and 22, timer 24 and gain control circuit 26 constitute a sensing threshold control means.

The first comparator pair circuit 20 comprises two comparators 30 and 32, receives as input the output of the amplifier 18 and produces a DETECT signal when the amplitude of the filtered and amplified cardiac signal is greater than VREF1. The DETECT signal is used to measure the cardiac cycle time which is the time interval between consecutive DETECT signals. The two comparators 30 and 32 provide for detection of the cardiac signals of both positive and negative polarities. The OR gate 34 operates on the output of the comparators 30 and 32.

Similarly, the second comparator pair circuit 22 comprises two comparators 40 and 42, and an OR gate 44. The comparator pair circuit 22 produces a GAIN DOWN signal when the amplitude of the filtered and amplified cardiac signal is greater than VREF2. This is to effectively limit the peak of the amplified signal to +/−VREF2. Again, the two comparators 40 and 42 allow the system to regulate signals of both positive and negative polarities. The GAIN DOWN signal may be high or low, and is used to decrease the sensing threshold. GAIN DOWN is high when the amplitude of the filtered and amplified cardiac signal is greater than VREF2.

The gain control circuit 26 sets the gain of the amplifier 18 and is responsive to the timer 24. The timer 24 controls the interval following delivery of a pacing pulse during which the amplifier 18 is held at a fixed gain setting. Specifically, when a pacing pulse is delivered by the system 11, the timer 24 is triggered to output a high FIXED GAIN signal, reset and begin to run for a predetermined period of time called the fixed gain time interval. The FIXED GAIN signal remains high until the fixed gain time interval of the timer 24 has elapsed. For a discussion of gain control in probability density function detection, see U.S. Pat. No. 4,184,493 to Langer et al.

The gain control circuit 26 in the present invention operates as follows. If the FIXED GAIN signal is low and the GAIN DOWN signal is high, the gain control circuit 26 rapidly decreases the gain of the amplifier 18. This increases the sensing threshold when the amplified cardiac signal is above VREF2. If the FIXED GAIN and GAIN DOWN signals are both low, the gain control circuit 26 slowly increases the gain. This decreases the sensing threshold when the amplified cardiac signal is below VREF1 and VREF2. If the FIXED GAIN signal is high, the gain of the amplifier is set and held constant at a predetermined value. The sensing of the system at any given time is, sensing threshold(t)=−VREF1/GAIN(t).

In the system shown in FIG. 2, VREF2 is always greater than VREF1 so that the sensing threshold is automatically adjusted to a value less than the amplitude of the R-wave at any instant of time. Following a pacing pulse, the sensing threshold is set to a predetermined level and held at that level for a predetermined time interval. It is possible that an attending physician may adjust the fixed sensing threshold and the fixed sensitivity interval (fixed gain interval).

Figure 3:
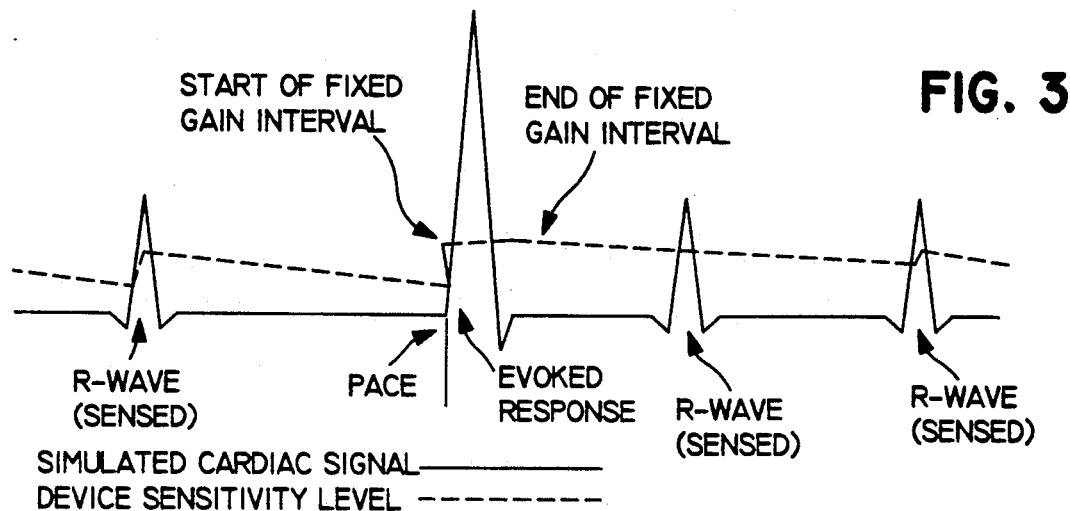
FIG. 3 is a graphical representation of the sensing threshold response in accordance with the present invention.
Figure 4:
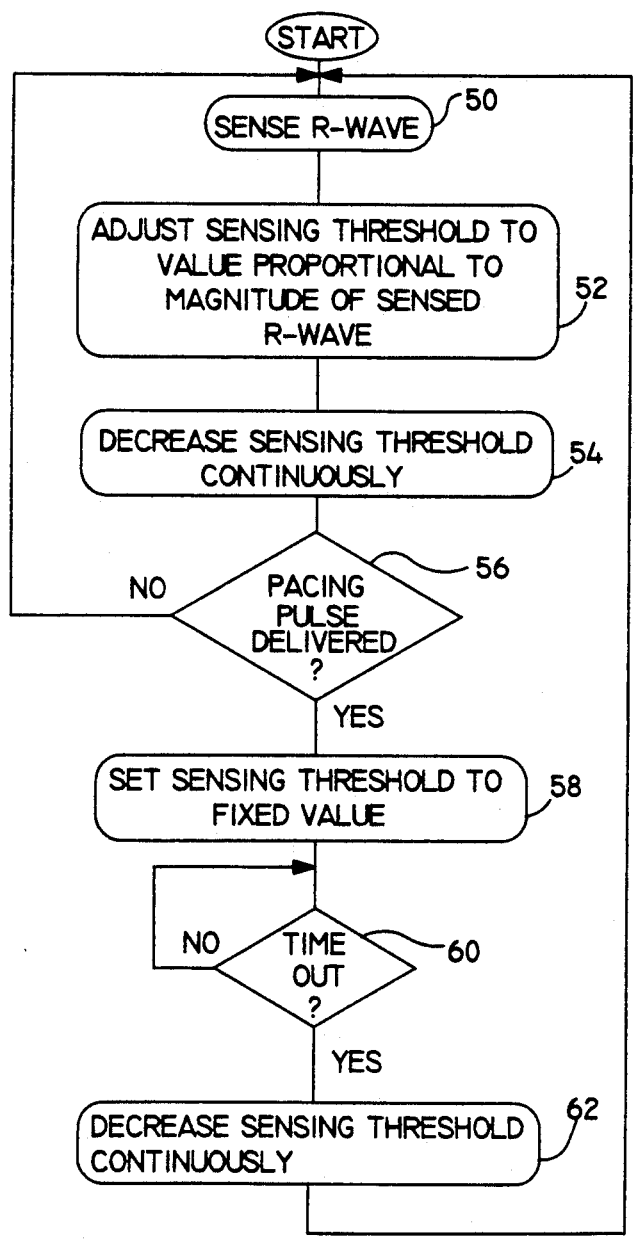
FIG. 4 is a flow chart illustrating the steps for controlling the sensing threshold according to the present invention.

Turning now to FIGS. 3 and 4, the operation of the system 10 will now be described with reference to the diagram of FIG. 3 and the flow chart of FIG. 4. Initially, assuming that a pacing pulse is not required, an R-wave is sensed in step 50. At that time, the sensing threshold has been set to a value proportional to the magnitude of the sensed cardiac signal in step 52. This is accomplishing by rapidly increasing the sensing threshold during the R-wave. The gain is rapidly decreased to the point where the amplified signal falls below VREF2, (FIG. 2). Thereafter, the sensing threshold is decreased continuously in step 54 until the next R-wave or until a pacing pulse is delivered.

In step 56, if a pacing pulse is not delivered, then the method returns to step 50 to detect the next R-wave. If a pacing pulse is delivered, the method continues to step 58 at which the sensing threshold is set to a fixed value for a fixed gain interval. After a period of time expires equal to the fixed gain interval as represented by step 60, the sensing threshold is allowed to decrease from the fixed level in step 62. Because of this decrease, the spontaneous R-wave immediately following the evoked R-wave is detected. In the implementation described it is possible for the filtered and amplifier signal peak to be between VREF 1 and VREF2, in which case the sensing threshold will not be increased for the R-Wave.

The comparator reference voltages VREF1 AND VREF2 may be adjusted to achieve relative changes in the sensing threshold instead of or in addition to changing the gain of the amplifier 18. In addition, the frequency response characteristics of the bandpass filter 16, the fixed gain setting and the fixed gain interval may be adjusted.

While the present invention has been described for use in detecting ventricular depolarizations, the same type of system may be used to detect atrial depolarizations.

The above description is intended by way of example only and is not intended to limit the present invention in any way except as set forth in the following claims.

We claim:

1. A method for automatically adjusting the sensing threshold in a cardioverter/defibrillator system with pacing capability, the method comprising the steps of:
    detecting the occurrence and magnitude of R-waves;
    adjusting a sensing threshold to a value proportional to a magnitude of a sensed R-wave;
    decreasing the sensing threshold from the value continuously until a next detected R-wave;
    delivering a pacing pulse to the heart;
    adjusting the sensing threshold to a fixed value for a predetermined period of time after delivery of the pacing pulse; and
    continuously decreasing the sensing threshold from the fixed value after the predetermined period of time until a next detected R-wave.

2. A method for automatically adjusting the sensing threshold in a cardioverter/defibrillator system with pacing capability, the method comprising the steps of adjusting the sensing threshold to a value proportional to a sensed cardiac signal for spontaneous cardiac depolarization and decreasing the sensing threshold continuously thereafter; and adjusting the sensing threshold to a fixed value for a predetermined period of time when a pacing pulse is delivered and decreasing the sensing threshold continuously after the predetermined period of time.

3. A system for automatically adjusting the sensing threshold in a cardioverter/defibrillator system with pacing capability, the system comprising:

detecting means for detecting cardiac signals;

amplifying means for amplifying cardiac signals according to a variable gain to generate amplified cardiac signals; and sensing threshold control means for controlling the gain of the amplifying means to set a sensing threshold, said sensing threshold control means responsive to spontaneous cardiac depolarizations to set the variable gain of the amplifying means to a level proportional to the magnitude of the spontaneous cardiac depolarizations and to continuously change the variable gain of the amplifying means so that the sensing threshold decreases continuously from a first maximum value until a next cardiac depolarization, said sensing threshold control means being further responsive to delivery of pacing pulses to the heart of the patient to set the variable gain of the amplifying means to a fixed sensing threshold for a predetermined period of time and to continuously change the variable gain of the amplifying means so that the sensing threshold decreases continuously from a second maximum value after the predetermined period of time.

4. The system of claim 3, wherein the sensing threshold control means comprises:

gain control means for adjusting the variable gain of the amplifying means;

timer means connected to the gain control means and responsive to delivery of a pacing pulse for counting a predetermined time interval and delivering a fixed gain signal to the gain control means during said predetermined time interval;

comparing means connected to said gain control means for comparing the output of the amplifying means and issuing a detect signal in the event that the output of the amplifying means exceeds a first predetermined threshold, said detect signal indicative of the occurrence of depolarizations of the heart, and issuing a gain down signal in the event that the output of the amplifying means exceeds a second predetermined reference level which is greater than said first predetermined reference level.

* * * * *